United States Patent
Miyazaki et al.

(10) Patent No.: US 12,020,466 B2
(45) Date of Patent: Jun. 25, 2024

(54) COMPUTER-READABLE RECORDING MEDIUM, TRAINING DATA GENERATION METHOD, AND TRAINING DATA GENERATION APPARATUS

(71) Applicant: FUJITSU LIMITED, Kawasaki (JP)

(72) Inventors: Nobuhiro Miyazaki, Kawasaki (JP); Hiroaki Takebe, Kawasaki (JP); Takayuki Baba, Kawasaki (JP); Masahiko Shimada, Sumida (JP)

(73) Assignee: FUJITSU LIMITED, Kawasaki (JP)

( * ) Notice: Subject to any disclaimer, the term of this patent is extended or adjusted under 35 U.S.C. 154(b) by 552 days.

(21) Appl. No.: 17/233,539

(22) Filed: Apr. 19, 2021

(65) Prior Publication Data

US 2021/0391060 A1 Dec. 16, 2021

(30) Foreign Application Priority Data

Jun. 15, 2020 (JP) .................. 2020-103246

(51) Int. Cl.
*G06V 10/00* (2022.01)
*G06T 7/00* (2017.01)
(Continued)

(52) U.S. Cl.
CPC .......... *G06V 10/443* (2022.01); *G06T 7/0012* (2013.01); *G06V 10/774* (2022.01);
(Continued)

(58) Field of Classification Search
CPC .... G06V 10/443; G06V 10/774; G16H 30/40; G06T 7/0012; G06T 2207/10081; G06T 2207/20081
See application file for complete search history.

(56) References Cited

U.S. PATENT DOCUMENTS

2019/0340735 A1 11/2019 Nishina
2020/0160977 A1 5/2020 Lyman et al.
(Continued)

FOREIGN PATENT DOCUMENTS

CN 101246549 B * 7/2012 ......... G06K 9/00449
JP 2015148986 A * 8/2015
(Continued)

OTHER PUBLICATIONS

Armanious, et al., "MedGAN: Medical image translation using GANs", Computerized Medical Imaging and Graphics, Pergamon Press, New York, NY, US, vol. 79, Nov. 22, 2019 (Nov. 22, 2019), XP086043780, 14 pp.
(Continued)

*Primary Examiner* — Khai M Nguyen
(74) *Attorney, Agent, or Firm* — XSENSUS LLP

(57) ABSTRACT

A non-transitory computer-readable storage medium storing a program that causes a computer to execute a process, the process includes identifying first filter processing applied to a first image that is training data used for machine learning; generating the first image from which characteristics of the identified first filter processing are removed; and generating, by applying second filter processing to the first image from which the characteristics are removed, a second image to be assigned a label identical to a label of the first image, the second image being used in the machine learning as the training data.

18 Claims, 12 Drawing Sheets

(51) Int. Cl.
  *G06V 10/44*  (2022.01)
  *G06V 10/774*  (2022.01)
  *G16H 30/40*  (2018.01)

(52) U.S. Cl.
  CPC ... *G16H 30/40* (2018.01); *G06T 2207/10081* (2013.01); *G06T 2207/20081* (2013.01)

(56) References Cited

U.S. PATENT DOCUMENTS

2020/0242404 A1* 7/2020 Teshima ................. G06V 10/82
2021/0390696 A1* 12/2021 Iwase ........................ G06T 5/60

FOREIGN PATENT DOCUMENTS

| JP | 2018-110714 A | | 7/2018 | | |
|---|---|---|---|---|---|
| JP | 2018110714 A | * | 7/2018 | ............... | A61B 6/03 |
| JP | 2018-180729 A | | 11/2018 | | |
| JP | 2019-56957 A | | 4/2019 | | |

OTHER PUBLICATIONS

Extended European Search Report dated Sep. 23, 2021, in corresponding European Patent Application No. 21168554.0.
"Understanding Respiratory Medicine with Pictogram" Available Online At: https://respiresi.exblog.jp/23965463/, Retrieved on Jun. 11, 2020, 5 pages including English Translation.
Miura et al., "Construction of Flower Image Dataset and Classification using Convolutional Neural Network", DEIM Forum 2017 C4-3, 2017, 18 pages including English Translation.
Dosovitskiy et al., "Unsupervised Feature Learning by Augmenting Single Images", arXiv:1312.5242v3, Feb. 16, 2014, pp. 1-7.
Japanese Office Action dated Oct. 17, 2023, in corresponding Japanese Application No. 2020-103246, 12pp.

* cited by examiner

FIG. 3

| FILE NAME | LINK | ID |
|---|---|---|
| Image1 | ¥¥//… | IMG1 |
| Image2 | ¥¥//… | IMG2 |
| … | … | … |

| IMAGING APPARATUS | RECONSTRUCTION FUNCTION | TIME DATA | LINK (TIME DATA) | FREQUENCY DATA | LINK (FREQUENCY DATA) | GENERATION |
|---|---|---|---|---|---|---|
| D1 | F1 | 0 | ¥¥//··· | 0 | ¥¥//··· | 1 |
| D1 | F3 | 1 | ¥¥//··· | 0 | ¥¥//··· | 0 |
| ⋮ | ⋮ | ⋮ | ⋮ | ⋮ | ⋮ | ⋮ |
| D2 | F2 | 0 | ¥¥//··· | 0 | ¥¥//··· | 0 |
| D2 | F4 | 1 | ¥¥//··· | 1 | ¥¥//··· | 1 |
| ⋮ | ⋮ | ⋮ | ⋮ | ⋮ | ⋮ | ⋮ |

| FILE NAME | LINK | ID |
|---|---|---|
| Image1_PSF1 | ¥¥//... | IMG1 |
| Image1_PSF2 | ¥¥//... | IMG1 |
| Image2_PSF1 | ¥¥//... | IMG2 |
| Image2_PSF3 | ¥¥//... | IMG2 |
| ... | ... | ... |

203

COMPUTER-READABLE RECORDING MEDIUM, TRAINING DATA GENERATION METHOD, AND TRAINING DATA GENERATION APPARATUS

CROSS-REFERENCE TO RELATED APPLICATION

This application is based upon and claims the benefit of priority of the prior Japanese Patent Application No. 2020-103246, filed on Jun. 15, 2020, the entire contents of which are incorporated herein by reference.

FIELD

The embodiment discussed herein is related to a computer-readable recording medium, a training data generation method, and a training data generation apparatus.

BACKGROUND

An improvement in efficiency of image-based medical diagnosis is desired since the burden on a doctor is increasing because of a shortage of doctors and an increase in the number of taken images per diagnosis. Reference to disease names and medical record information of past similar cases by a doctor expectedly decreases the time taken for an image-based diagnosis and improves the efficiency.

To enable reference to past similar cases, it is conceived to extract features of a case from an image through machine learning or the like and to search for past similar cases based on the features. On the other hand, with machine learning for extracting features of a case in an image, classifying an image not included in training may fail. Therefore, for computed tomography (CT) images having different image qualities due to differences in imaging conditions, it is desired to generate a large number of pairs of correct labels and images of various variations imaged under expected imaging conditions.

As a method of generating a large number of pairs of images and correct labels, a method is conceivable in which a doctor manually creates correct labels of cases in CT images based on knowledge. There is also known a method of generating images of various variations by performing image processing such as rotation, inversion, translation, scale change, color change, and contrast change on training data already assigned a correct label. For example, Japanese Laid-open Patent Publication No. 2018-180729; Japanese Laid-open Patent Publication No. 2019-56957; "Understanding Respiratory Medicine with Pictogram (Piku-toguramu de Wakaru Kokyuki Naika)", (https://respiresi.ex-blog.jp/23965463/); MIURA Kenta and KIDA Takuya, "Construction of Flower Image Dataset and Classification using Convolutional Neural Network (Nana Gazo Detasetto no Kochiku to Tatamikomi Nyuraru Nettowaku ni yoru Bunrui)", DEIM Forum 2017, 2017; A. Dosovitskiy, J. T. Springenberg, and T. Brox, "Unsupervised feature learning by augmenting single images", arXiv, 2014; and the like are disclosed.

SUMMARY

According to an aspect of the embodiments, a non-transitory computer-readable storage medium storing a program that causes a computer to execute a process, the process includes identifying first filter processing applied to a first image that is training data used for machine learning; generating the first image from which characteristics of the identified first filter processing are removed; and generating, by applying second filter processing to the first image from which the characteristics are removed, a second image to be assigned a label identical to a label of the first image, the second image being used in the machine learning as the training data.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 3 is a diagram illustrating an example of a data structure of training data information;

FIG. 4 is a diagram illustrating an example of a data structure of imaging condition information;

FIG. 5 is a diagram illustrating an example of a data structure of generation data information;

DESCRIPTION OF EMBODIMENTS

However, the methods of the related art have an issue in that pairs of suitable training images and correct labels may not be efficiently generated. For example, the method in which a doctor manually creates a correct label involves manual work and also involves preparation of a sufficient quantity of images in advance. Thus, pairs of images and correct labels may not be efficiently generated. In the method of generating images by image processing, an image that is unlikely to exist as a taken image may be generated. Thus, classification accuracy may not be improved.

In view of the above, it is desirable to efficiently generate pairs of suitable training images and correct labels.

An embodiment will be described below. Note that the present disclosure is not limited to this embodiment. The embodiment may be combined with another embodiment as appropriate within a scope without any contradiction.

Embodiment

Figure 1:
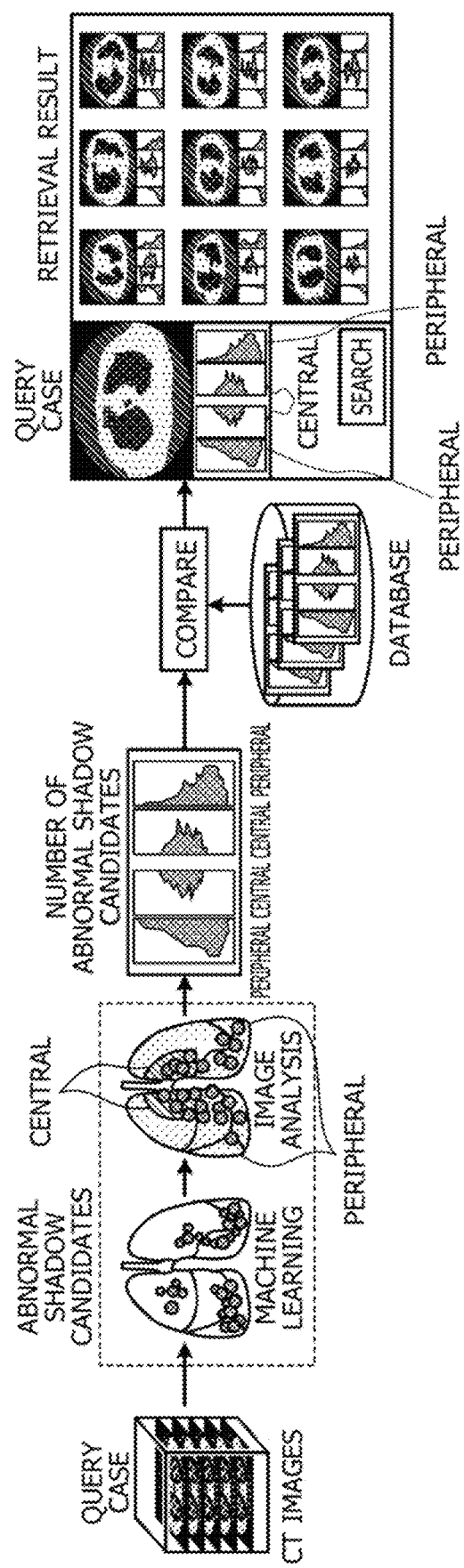
FIG. 1 is a diagram for describing a similar case search method.

First, a similar case search based on CT images will be described using to FIG. 1. As illustrated in FIG. 1, from CT images serving as a query case, abnormal shadow candidates are extracted with a machine-learning-based method and image analysis. The extracted abnormal shadow candidates are compared with data of shadows of past cases stored in a database. A list of images similar to the query case is obtained as a retrieval result.

Figure 2:
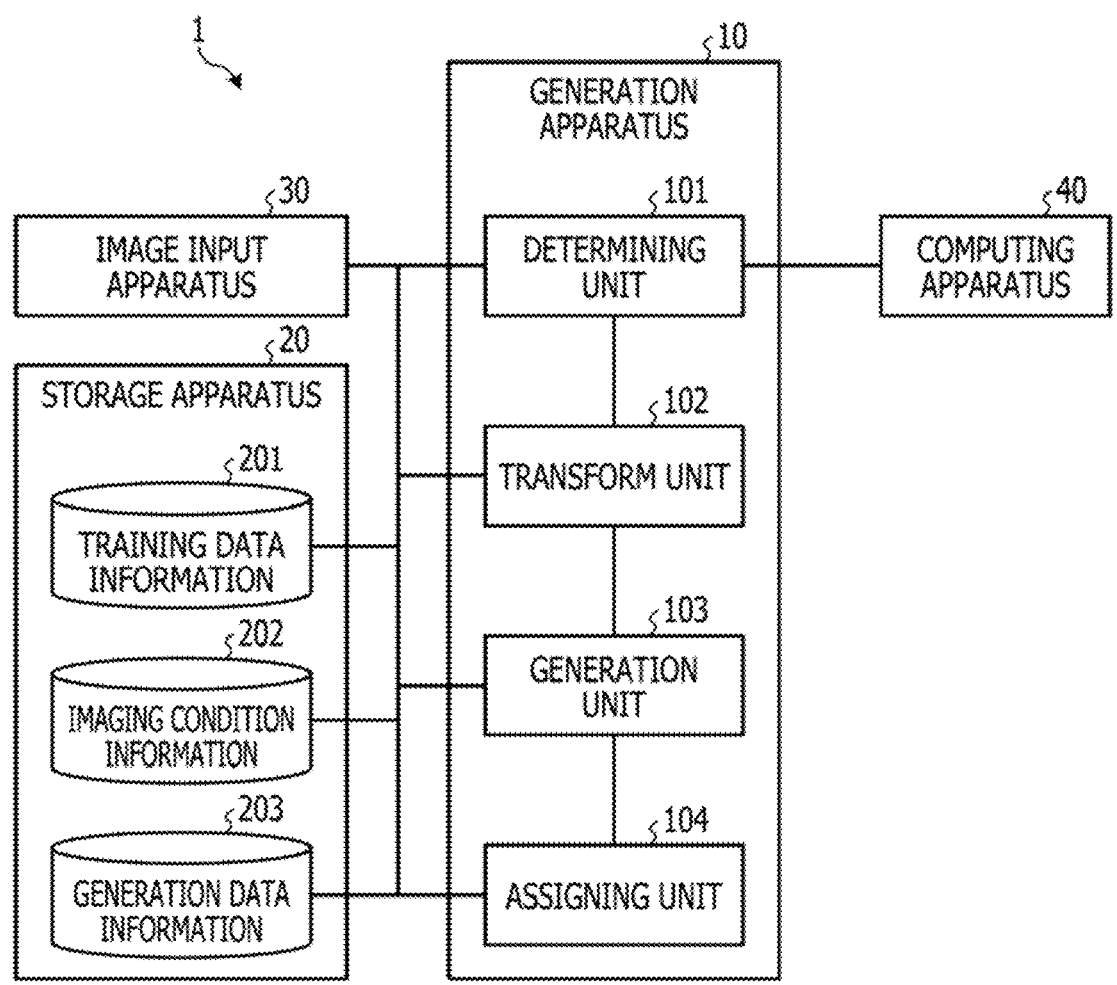
FIG. 2 is a diagram illustrating an example of a configuration of a generation system.

FIG. 2 is a diagram illustrating an example of a configuration of a generation system. As illustrated in FIG. 2, a generation system 1 includes a generation apparatus 10, a storage apparatus 20, an image input apparatus 30, and a computing apparatus 40. For example, the computing apparatus 40 is a terminal such as a personal computer operated by a user. For example, the generation apparatus 10, the storage apparatus 20, and the image input apparatus 30 are servers. Some or all of functions of the individual apparatuses of the generation system 1 may be integrated.

As illustrated in FIG. 2, based on images input from the image input apparatus 30, the generation apparatus 10 generates pairs of training images and correct labels. At this time, the generation apparatus 10 refers to information stored in the storage apparatus 20 as appropriate. The generation apparatus 10 may perform a process in accordance with an operation performed via the computing apparatus 40.

The generation apparatus 10 includes a determining unit 101, a transform unit 102, a generation unit 103, and an assigning unit 104. The storage apparatus 20 stores training data information 201, imaging condition information 202, and generation data information 203.

The training data information 201 includes information on an existing training image. For example, an existing training image is data of an image actually taken by a CT apparatus or the like and to which a reconstruction function is applied.

FIG. 3 is a diagram illustrating an example of a data structure of the training data information. As illustrated in FIG. 3, the training data information 201 includes a file name, a link, and an identifier (ID). The file name is the name of an image file. The link is a path of a storage location of the image file. The ID is an index for associating the image with a generated image. The generation of the image will be described later. For example, in the example illustrated in FIG. 3, the ID of an image file named "Image1" is "IMG1".

The imaging condition information 202 includes information on imaging conditions. For example, the imaging conditions are the type of the CT apparatus used for taking an image and a reconstruction function. The imaging conditions may include a tube voltage or the like.

FIG. 4 is a diagram illustrating an example of a data structure of the imaging condition information. As illustrated in FIG. 4, the imaging condition information 202 includes an imaging apparatus, a reconstruction function, time data, a link (time data), frequency data, a link (frequency data), and generation. The imaging apparatus and the reconstruction function correspond to imaging conditions. The time data is a flag for managing the presence or absence of the PSF in the time domain. The link (time data) is a storage location of the PSF data in the time domain. The frequency data is a flag for managing the presence or absence of the PSF in the frequency domain. The link (frequency data) is a storage location of the PSF data in the frequency domain. The storage location may be a location where data is actually stored or a location where, if corresponding data is to be generated, the data is to be stored. Generation is a flag for managing the use of the PSF in generation of training data. For example, in the example illustrated in FIG. 4, there are no time data and frequency data for the imaging apparatus of "D1" and the reconstruction function of "F1". Thus, the time data and the frequency data are imaging conditions to be used in generation of data.

FIG. 5 is a diagram illustrating an example of a data structure of the generation data information. As illustrated in FIG. 5, the generation data information 203 includes a file name, a link, and an ID. The file name is the name of an image file. The link is a path of a storage location of the image file. The ID is an index for associating the image with a generated image. For example, in the example illustrated in FIG. 5, the ID of an image file named "Image1_PSF1" is "IMG1".

Figure 6:
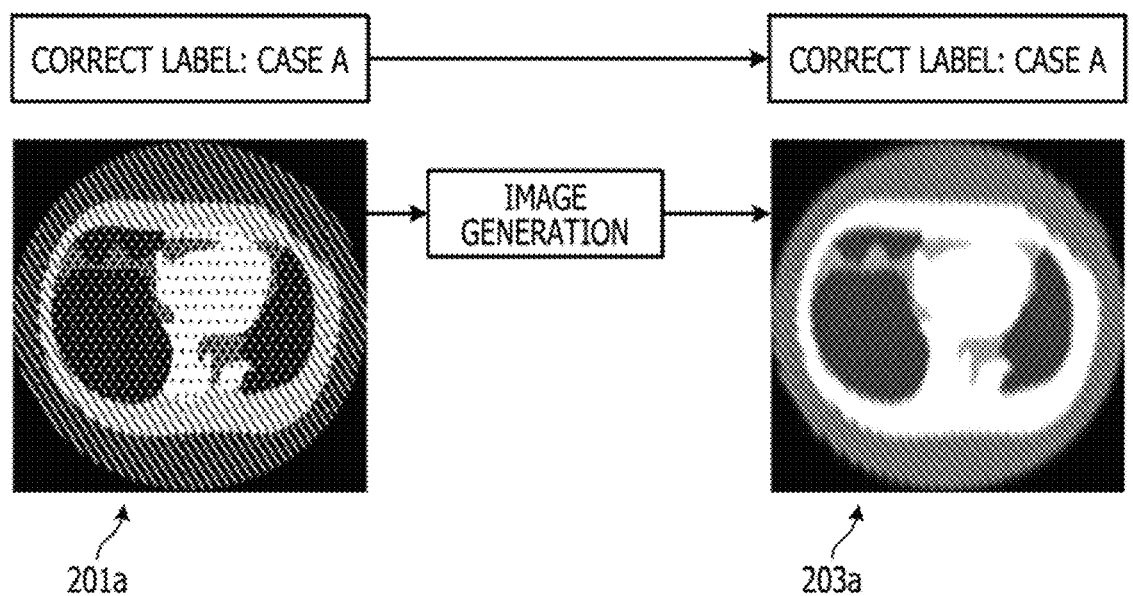
FIG. 6 is a diagram for describing a method of generating a pair of an image and a correct label.

FIG. 6 is a diagram for describing a method of generating a pair of an image and a correct label. As illustrated in FIG. 6, the generation apparatus 10 performs image generation based on an existing training image 201a and generates an image 203a. At this time, the generation apparatus 10 assigns, to the image 203a, the same correct label as the correct label assigned to the image 201a. Details of each processing unit, of the generation apparatus 10, for generating a pair of an image and a correct label will be described below.

The determining unit 101 determines a first filter applied to a first image. The first image is an existing training image. The determining unit 101 acquires information on the first image from the training data information 201.

The filter used in the present embodiment is a PSF. The PSF is applied to an image by a convolution operation. Therefore, for example, the determining unit 101 determines a first PSF applied to the first image by a convolution operation.

The PSF is associated with the imaging conditions. The imaging conditions include the type of the imaging apparatus and the reconstruction function. Thus, for example, the determining unit 101 determines the first filter associated with a first imaging condition that is an imaging condition of the first image. The determining unit 101 determines the first filter associated with the first imaging condition that is a combination of the imaging apparatus and the reconstruction function used for the first image.

For example, the determining unit 101 may extract the imaging apparatus name (type) and the reconstruction function from a tag attached to a Digital Imaging and Communications in Medicine (DICOM) image. The manufacturer's model name of the DICOM tag (0008, 1090) corresponds to the imaging apparatus name. The convolution kernel of the DICOM tag (0018, 1210) corresponds to the reconstruction function.

The list of the reconstruction functions for respective imaging apparatuses may be input to the generation apparatus 10 by a user via the computing apparatus 40. For example, the user inputs that reconstruction functions F1 and F3 are used for an imaging apparatus D1. For example, the user inputs that reconstruction functions F2 and F4 are used for an imaging apparatus D2.

The determining unit 101 is capable of determining the PSF by imaging a metallic wire (phantom) (reference literature: ICHIKAWA Katsuhiro, HARA Takanori, NIWA Shinji, and OHASHI Kazuya, "Method of Measuring Modulation Transfer Function Using Metal Wire in Computed Tomography", Japanese Journal of Radiological Technology, 2008). The determining unit 101 is capable of determining the PSF using blood vessels in a CT image (reference literature: KAWATA Yoshiki, NAKAYA Yoshihiro, NIKI Noboru, OHMATSU Hironobu, EGUCHI Kenji, KANEKO Masahiro, and MORIYAMA Noriyuki, "A Measurement Method of Point Spread Functions from CT Images", The IEICE transactions on information and systems (Japanese edition), 2008).

The determining unit 101 determines a PSF to be used in generation of data. As data used as training data, images of various variations are suitable. The variations (for example, differences in image quality) change depending on the shape of the PSF. Therefore, data coverage may be improved by generating an image with a PSF different from (not similar to) the PSF associated with the imaging conditions of the existing training image. Thus, the determining unit 101 determines a PSF for which a similarity in distribution between the PSF associated with the imaging conditions of the existing training image and the PSF associated with the imaging conditions of an image to be generated is less than or equal to a certain threshold.

The determining unit 101 determines the PSF for each target to be identified. For example, as for medical images for which image data is difficult to collect, there may be a bias in imaging conditions for each case. Thus, generation of training data using the same PSF for all targets to be identified is not necessarily suitable.

It is assumed that there are PSF1, PSF2, and PSF3 with distributions different from each other, and that training data of a case A include PSF1 and PSF2 and training data of a case B include PSF1 and PSF3. In this case, generation of training data with the PSF3 is suitable for the case A, and generation of training data with the PSF2 is suitable for the case B. The similarity in distribution between the PSFs may be calculated using, for example, a normalized cross-correlation function R represented by Equation (1).

$$R = \frac{\sum_{y=0}^{h-1}\sum_{x=0}^{w-1} I(x,y)T(x,y)}{\sqrt{\sum_{y=0}^{h-1}\sum_{x=0}^{w-1} I(x,y)^2 \sum_{y=0}^{h-1}\sum_{x=0}^{w-1} T(x,y)^2}} \quad (1)$$

I(x, y) denotes a PSF used as existing training data. T(x, y) denotes a PSF of training data to be generated. h denotes the height of the PSF. w denotes the width of the PSF.

The transform unit 102 transforms the PSF or image in the time domain into that in the frequency domain by Fourier transform. The transform unit 102 transforms the PSF or image in the frequency domain into that in the time domain by Fourier transform.

The transform unit 102 transforms I(x, y), which is an image in the time domain, into that in the frequency domain as represented by Equation (2). F{ } denotes Fourier transform.

$$F\{I(x,y)\} = \sum_{n_1=-\infty}^{\infty}\sum_{n_2=-\infty}^{\infty} I(n_1,n_2)e^{(-j\omega_1 n_1)}e^{(-j\omega_2 n_2)} \quad (2)$$

The transform unit 102 transforms P(x, y), which is a PSF in the time domain, into that in a frequency domain as represented by Equation (3).

$$F\{P(x,y)\} = \sum_{n_1=-\infty}^{\infty}\sum_{n_2=-\infty}^{\infty} P(n_1,n_2)e^{(-j\omega_1 n_1)}e^{(-j\omega_2 n_2)} \quad (3)$$

The generation unit 103 generates a second image obtained by applying a second filter to the first image in which characteristics of the first filter are canceled. For example, the generation unit 103 generates, as the second image, an image obtained by transforming, by inverse Fourier transform into the time domain, a result obtained by applying, by multiplication, a second PSF transformed into the frequency domain by Fourier transform, to the first image that is transformed into the frequency domain by Fourier transform and in which the characteristics of the first PSF are canceled by multiplication.

Let I(x, y) denote a CT image. Let O(x, y) denote image data before applying PSF. Let P(x, y) denote the PSF. In this case, I(x, y) is represented by Equation (4). Note that * is a convolution operator (filtering processing).

$$I(x,y)=O(x,y)*P(x,y) \quad (4)$$

The generation unit 103 generates F(I'(x, y)) using Equation (5). F(I'(x, y)) denotes a result obtained by applying, by multiplication, the second PSF transformed into the frequency domain by Fourier transform, to the first image that is transformed into the frequency domain by Fourier transform and in which the characteristics of the first PSF are canceled by multiplication.

$$F\{I'(x,y)\} = F\{O(x,y)\} \cdot F\{P(x,y)\} \cdot \frac{1}{F\{P(x,y)\}} \cdot F\{P'(x,y)\} \quad (5)$$

F{P(x, y)}/F{P(x, y)} indicates cancellation of the imaging conditions (PSF). Multiplication by F{P(x, y)} or F{P'(x, y)} indicates application of the PSF. In this manner, the convolution operation in the time domain may be expressed by multiplication in the frequency domain.

The generation unit 103 generates the second image I'(x, y) using Equation (6). I'(x, y) denotes an image obtained by transforming F(I'(x, y)) into that in a time domain by inverse Fourier transform.

$$I'(x,y)=F^{-1}\{F\{I'(x,y)\}\} \quad (6)$$

The PSF is an example of a filter. The PSF corresponds to the imaging conditions. Therefore, the generation unit 103 generates, as the second image, an image obtained by applying the second filter associated with a second imaging condition different from the first imaging condition, to the first image in which the characteristics of the first filter are canceled.

The imaging conditions may be, for example, a combination of the imaging apparatus and the reconstruction function. Therefore, the generation unit 103 generates, as the second image, an image obtained by applying the second filter associated with the second imaging condition that is a combination of an imaging apparatus and a reconstruction function and is different from the first imaging condition, to the first image in which the characteristics of the first filter are canceled.

The assigning unit 104 assigns, to the second image, the correct label, for machine learning, assigned to the first image. The assigning unit 104 assigns, to the second image, a correct label corresponding to a case and assigned to the first image that is a CT image of a human body. For example, as illustrated in FIG. 6, if the correct label assigned to the existing training image 201*a* is "case A", the assigning unit 104 also assigns the correct label "case A" to the image 203*a* generated by the generation unit 103.

Figure 7:
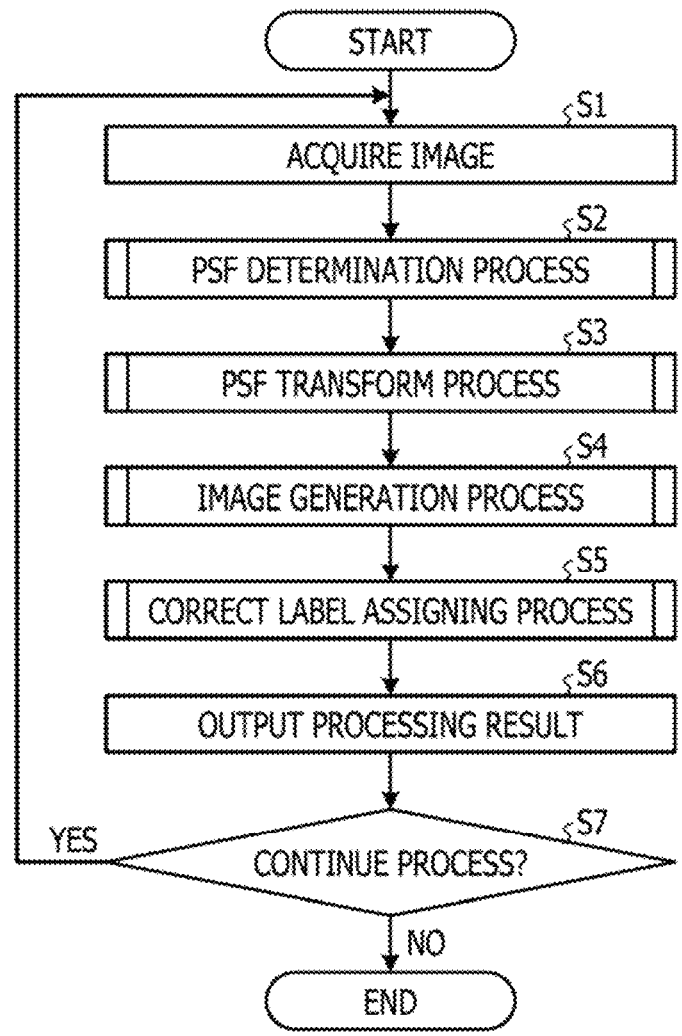
FIG. 7 is a flowchart illustrating a flow of a process of a generation apparatus.

FIG. 7 is a flowchart illustrating a flow of a process of the generation apparatus. As illustrated in FIG. 7, the generation apparatus 10 first acquires an image (step S1). In this example, the generation apparatus 10 acquires an existing training image assigned a correct label.

The generation apparatus 10 subsequently performs a PSF determination process (step S2). The generation apparatus 10 then performs a PSF transform process (step S3). The generation apparatus 10 performs an image generation process (step S4). The generation apparatus 10 performs a correct label assigning process (step S5). The generation apparatus 10 then outputs a processing result (step S6).

If a condition to continue the process is satisfied (Yes in step S7), the generation apparatus 10 causes the process to return to step S1 and repeats the processing. If the condition to continue the process is not satisfied (No in step S7), the generation apparatus 10 ends the process. For example, the condition to continue the process is that a predetermined number of images are not generated.

Figure 8:
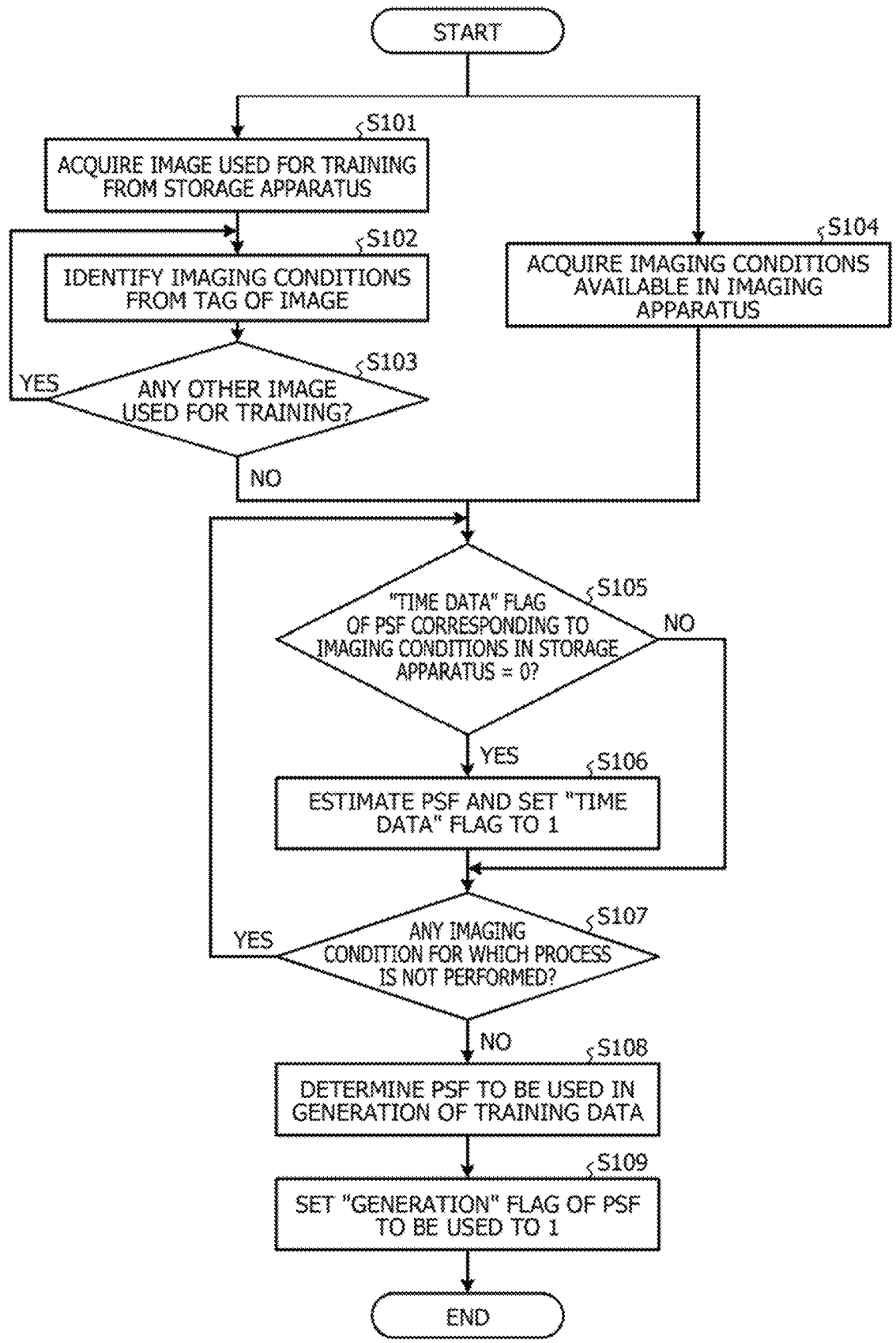
FIG. 8 is a flowchart illustrating a flow of a point spread function (PSF) determination process.

FIG. 8 is a flowchart illustrating a flow of the PSF determination process. The process in FIG. 8 corresponds to the PSF determination process (step S2) in FIG. 7. First, the determining unit 101 acquires an image used for training from the storage apparatus 20 (step S101). The determining unit 101 subsequently identifies the imaging conditions from the tag of the image (step S102). For example, the image, used for training, stored in the storage apparatus 20 is an existing training image that is taken by a CT apparatus and to which a reconstruction function is applied.

If there is another image to be used for training (Yes in step S103), the determining unit 101 causes the process to return to step S102 and repeats the processing. On the other hand, if there is no other image to be used for training (No in step S103), the determining unit 101 causes the process to proceed to step S105. In parallel with steps S101 to S103, the determining unit 101 acquires the imaging conditions available in an imaging apparatus (step S104).

If the "time data" flag of the PSF corresponding to the imaging conditions in the storage apparatus 20 is 0 (Yes in step S105), the determining unit 101 determines the PSF and sets the "time data" flag to 1 (step S106). On the other hand, if the "time data" flag of the PSF corresponding to the imaging conditions in the storage apparatus 20 is not 0 (No in step S105), the determining unit 101 causes the process to proceed to step S107.

If there is an imaging condition for which the process is not performed (Yes in step S107), the determining unit 101 causes the process to return to step S105 and repeats the processing. On the other hand, if there is no imaging condition for which the process is not performed (No in step S107), the determining unit 101 determines the PSF used in generation of training data (step S108). The determining unit 101 sets the "generation" flag of the PSF to be used to 1 (step S109).

Figure 9:
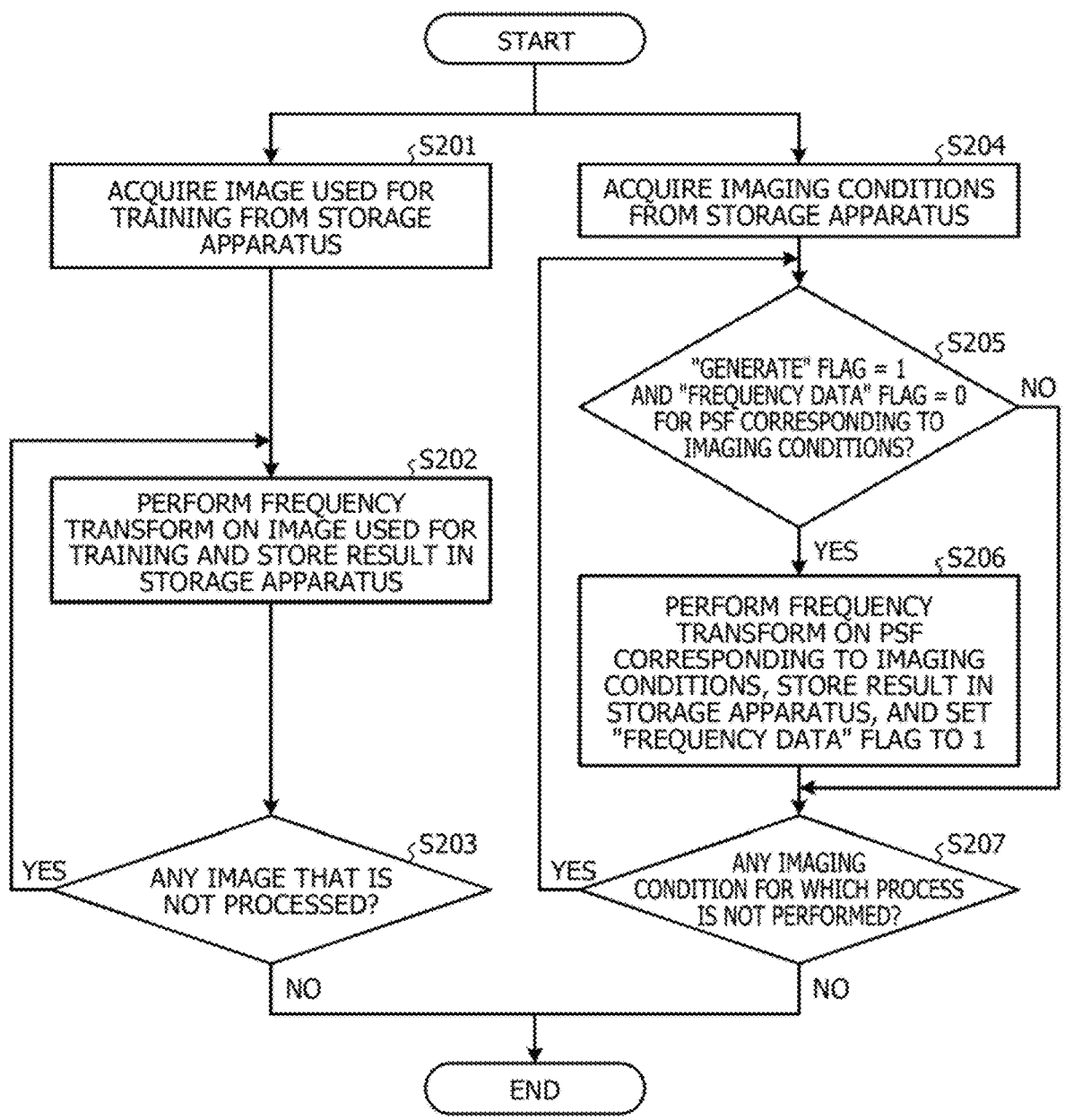
FIG. 9 is a flowchart illustrating a flow of a PSF transform process.

FIG. 9 is a flowchart illustrating a flow of the PSF transform process. The process in FIG. 9 corresponds to the PSF transform process (step S3) in FIG. 7. First, the transform unit 102 acquires an image used for training from the storage apparatus 20 (step S201). The transform unit 102 performs frequency transform on the image used for training and stores the result in the storage apparatus 20 (step S202).

If there is an image that is not processed (Yes in step S203), the transform unit 102 causes the process to return to step S202 and repeats the processing. On the other hand, if there is no image that is not processed (No in step S203), the transform unit 102 ends the process.

The transform unit 102 performs the following processing in parallel with steps S201 to S203. First, the transform unit 102 acquires imaging conditions from the storage apparatus 20 (step S204). If the "generation" flag and the "frequency data" flag of the PSF corresponding to the imaging conditions are 1 and 0, respectively, (Yes in step S205), the transform unit 102 causes the process to proceed to step S206. On the other hand, if the "generation" flag of the PSF corresponding to the imaging conditions is not 1 or the "frequency data" flag of the PSF is not 0 (No in step S205), the transform unit 102 causes the process to proceed to step S207.

The transform unit 102 performs frequency transform on the PSF corresponding to the imaging conditions, stores the result in the storage apparatus 20, and sets the "frequency data" flag to 1 (step S206). The PSF already transformed into the frequency domain and stored at this time is hereinafter referred to as frequency data. If there is an imaging condition for which the process is not performed (Yes in step S207), the transform unit 102 causes the process to return to step S205 and repeats the processing. On the other hand, if there is no imaging condition for which the process is not performed (No in step S207), the transform unit 102 ends the process.

Figure 10:
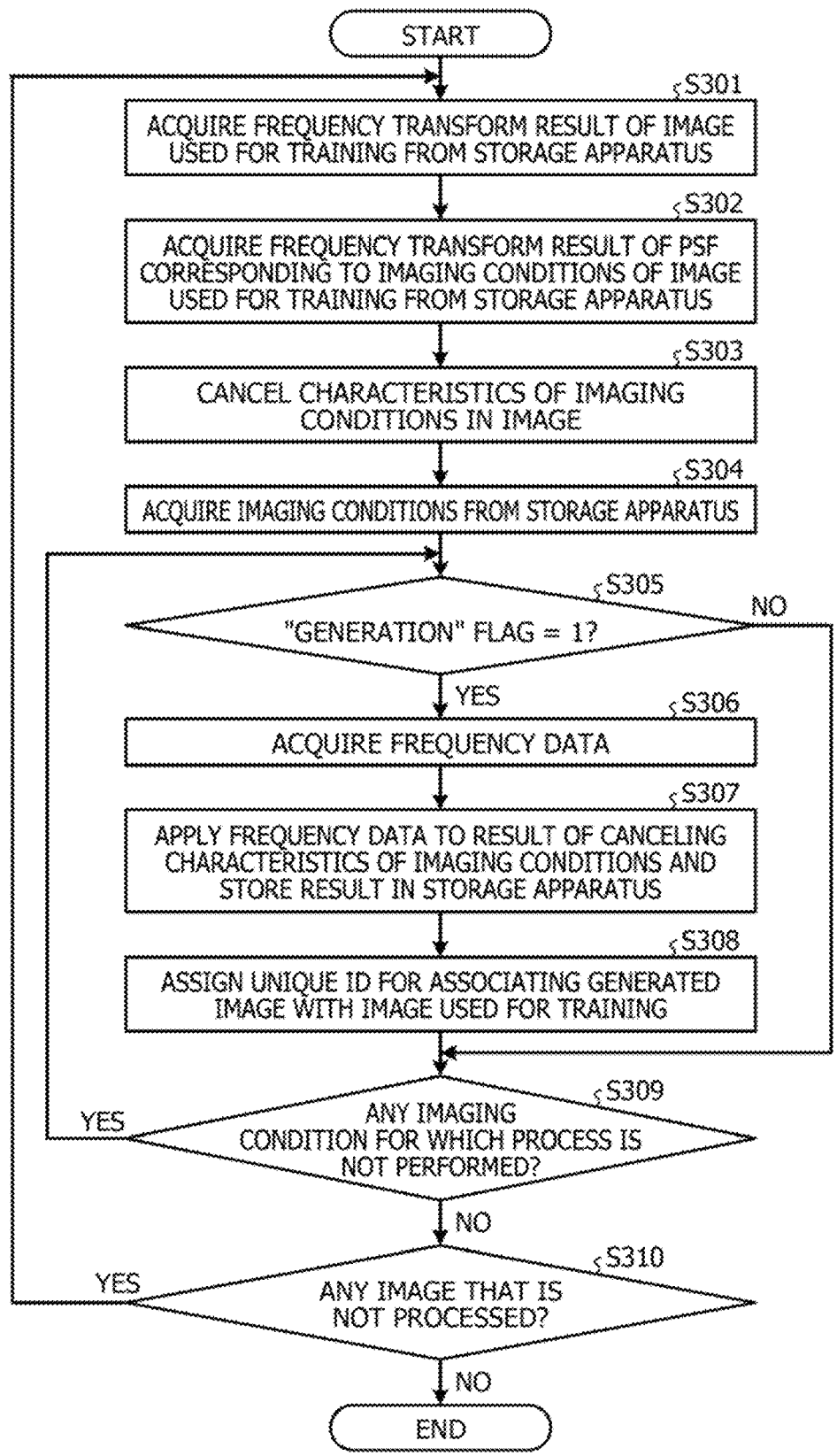
FIG. 10 is a flowchart illustrating a flow of an image generation process.

FIG. 10 is a flowchart illustrating a flow of the image generation process. The process in FIG. 10 corresponds to the image generation process (step S4) in FIG. 7. First, the generation unit 103 acquires a frequency transform result of the image used for training from the storage apparatus 20 (step S301). The generation unit 103 acquires, from the storage apparatus 20, the frequency transform result of the PSF corresponding to the imaging conditions of the image used for training (step S302).

The generation unit 103 cancels the characteristics of the imaging conditions in the image (step S303). If the PSF and the image are already transformed into the frequency domain, the generation unit 103 may cancel the characteristics of the imaging conditions and apply the frequency data by multiplications. The generation unit 103 acquires the imaging conditions from the storage apparatus 20 (step S304).

If the "generation" flag is not 1 (No in step S305), the generation unit 103 causes the process to proceed to step S309. On the other hand, if the "generation" flag is 1 (Yes in step S305), the generation unit 103 acquires the frequency data (step S306). The generation unit 103 then applies the frequency data to the result of canceling the characteristics of the imaging conditions and stores the result in the storage apparatus 20 (step S307). The generation unit 103 assigns a unique ID for associating the generated image with the image used for training (step S308).

If there is an imaging condition for which the process is not performed (Yes in step S309), the generation unit 103 causes the process to return to step S305 and repeats the processing. On the other hand, if there is no imaging condition for which the process is not performed (No in step S309), the generation unit 103 causes the process to proceed to step S310.

If there is an image that is not processed (Yes in step S310), the generation unit 103 causes the process to return to step S301 and repeats the processing. On the other hand, if there is no image that is not processed (No in step S310), the generation unit 103 ends the process.

Figure 11:
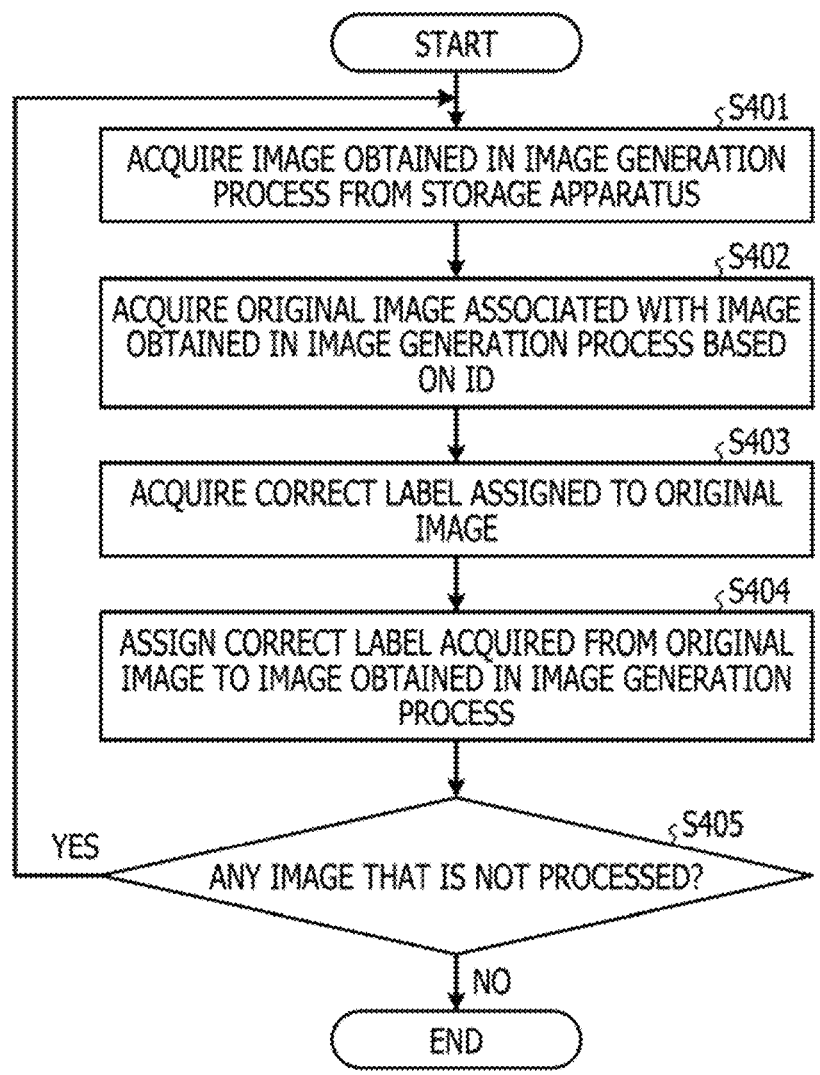
FIG. 11 is a flowchart illustrating a flow of a correct label assigning process.

FIG. 11 is a flowchart illustrating a flow of the correct label assigning process. The process in FIG. 11 corresponds to the correct label assigning process (step S5) in FIG. 7. First, the assigning unit 104 acquires the image obtained in the image generation process from the storage apparatus 20 (step S401). Based on the ID, the assigning unit 104 acquires the original image associated with the image obtained in the image generation process (step S402). The assigning unit 104 acquires the correct label assigned to the original image (step S403).

The assigning unit 104 assigns, to the image obtained in the image generation process, the correct label acquired from the original image (step S404). If there is an image that is not processed (Yes in step S405), the assigning unit 104 causes the process to return to step S401 and repeats the processing. On the other hand, if there is no image that is not processed (No in step S405), the assigning unit 104 ends the process.

As described above, the determining unit 101 determines the first filter applied to the first image. The generation unit 103 generates the second image obtained by applying the second filter to the first image in which the characteristics of the first filter are canceled. As described above, based on an existing image, the generation apparatus 10 automatically generates an image to which a different filter is applied. As a result, according to the present embodiment, pairs of suitable training images and correct labels may be efficiently generated.

For example, in a case where the present embodiment is applied to a CT image, a cost of generating data by manual work of a doctor may be reduced. For example, even in a case where there are a small number of images taken under imaging conditions desirably used as training data or where there is no such images, training data may be generated. High classification accuracy may be obtained for images taken under different imaging conditions.

The determining unit 101 determines the first PSF applied to the first image by a convolution operation. The generation unit 103 generates, as the second image, an image obtained by transforming, by inverse Fourier transform into the time domain, a result obtained by applying, by multiplication, the second PSF transformed into the frequency domain by Fourier transform, to the first image that is transformed into the frequency domain by Fourier transform and in which the characteristics of the first PSF are canceled by multiplication. As described above, by performing the frequency transform, cancellation of a filter applied by a convolutional operation or reapplication of a filter may be easily performed by multiplication.

The determining unit 101 determines the first filter associated with the first imaging condition that is the imaging condition of the first image. The generation unit 103 generates, as the second image, an image obtained by applying the second filter associated with the second imaging condition different from the first imaging condition, to the first image in which the characteristics of the first filter are canceled. Thus, images of the same imaging target under different imaging conditions may be easily generated.

The determining unit 101 determines the first filter associated with the first imaging condition that is a combination of the imaging apparatus and the reconstruction function used for the first image. The generation unit 103 generates, as the second image, an image obtained by applying the second filter associated with a second imaging condition that is a combination of an imaging apparatus and a reconstruction function and is different from the first imaging condition, to the first image in which the characteristics of the first filter are canceled. Thus, training images may be easily obtained even in a field, such as a medical field, where it is difficult to obtain training data.

The assigning unit 104 assigns, to the second image, the correct label, for machine learning, assigned to the first image. Thus, training data of different images having a common correct label may be generated.

The assigning unit 104 assigns, to the second image, a correct label corresponding to a case and assigned to the first image that is a CT image of a human body. Thus, an image of the same case as that of the existing image may be generated without actually performing imaging.

It is proved that the convolution operation in the time domain may be represented by multiplication in the frequency domain as represented in Equation (7).

$$F\{f*g\}=F\{f\}F\{g\} \quad (7)$$

First, the convolution operation is defined by Equation (8).

$$f*g[n] = \sum_{k=-\infty}^{\infty} f[k]g[n-k] \quad (8)$$

Discrete-time Fourier transform is defined by Equation (9).

$$F\{f\} = \sum_{n=-\infty}^{\infty} f[n]e^{-j\omega n} \quad (9)$$

At this time, it is proved by Equation (10) that the convolution operation transformed by the discrete-time Fourier transform is expressed by multiplication.

$$\begin{aligned} F\{f*g\} &= \sum_{n=-\infty}^{\infty} \left( \sum_{k=-\infty}^{\infty} f[k]g[n-k] \right) e^{-j\omega n} \\ &= \sum_{k=-\infty}^{\infty} f[k] \left( \sum_{n=-\infty}^{\infty} g[n-k]e^{-j\omega n} \right) \\ &= \sum_{k=-\infty}^{\infty} f[k] \left( \sum_{n'=-\infty}^{\infty} g[n']e^{-j\omega(n'+k)} \right) \\ &= \sum_{k=-\infty}^{\infty} f[k] \left( \sum_{n'=-\infty}^{\infty} g[n']e^{-j\omega n'} \right) e^{-j\omega k} \\ &= \sum_{k=-\infty}^{\infty} f[k]F\{g\}e^{-j\omega k} \\ &= \sum_{k=-\infty}^{\infty} f[k]e^{-j\omega k}F\{g\} \\ &= F\{f\}F\{g\} \end{aligned} \quad (10)$$

Processing procedures, control procedures, specific names, and information including various kinds of data and parameters described in the above specification and the drawings may be changed arbitrarily unless otherwise specified. The specific examples, distributions, numerical values, and the like described in the embodiment are merely examples, and may be changed arbitrarily.

The constituent elements in each of the apparatuses illustrated in the drawings are conceptually functional ones and are not necessarily configured physically as illustrated in the drawings. For example, specific forms of separation and integration of each of the apparatuses are not limited to those illustrated in the drawings. For example, all or some of the apparatuses may be configured to be distributed or integrated functionally or physically in arbitrary units depending on various loads, usage conditions, and so on. All or arbitrary part of processing functions performed by the respective apparatuses may be implemented by a central processing unit (CPU) and a program to be analyzed and executed by the CPU, or may be implemented as hardware by wired logic.

Figure 12:
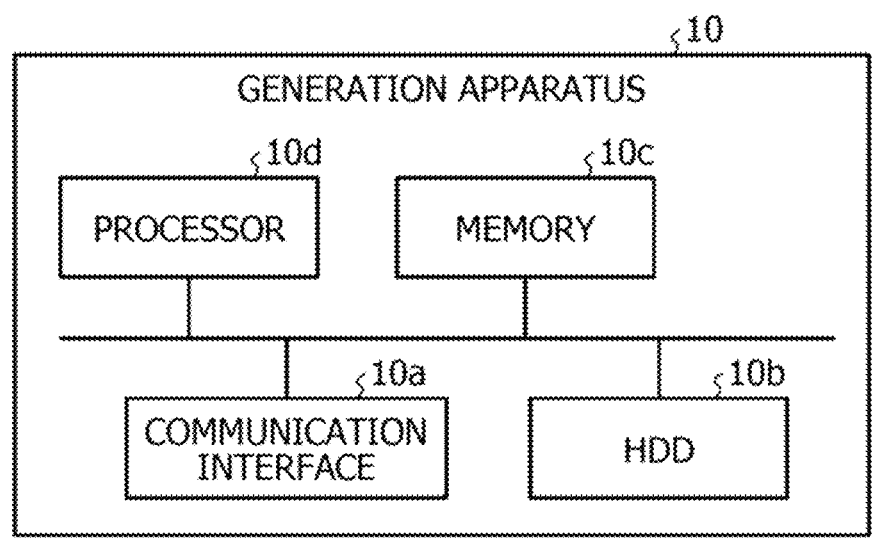
FIG. 12 is a diagram for describing an example of a hardware configuration.

FIG. 12 is a diagram for describing an example of a hardware configuration. As illustrated in FIG. 12, the generation apparatus 10 includes a communication interface 10a, a hard disk drive (HDD) 10b, a memory 10c, and a processor 10d. The individual components illustrated in FIG. 12 are coupled to each other by a bus or the like.

The communication interface 10a is a network interface card or the like and communicates with other servers. The HDD 10b stores the database and a program for causing the functions illustrated in FIG. 2 to operate.

The processor 10d is a hardware circuit that causes a process of executing each function described in FIG. 2 or the like to run, by reading a program for executing processing similar to that of each processing unit illustrated in FIG. 2 from the HDD 10b or the like and loading the program to the memory 10c. For example, this process executes a function similar to that of each processing unit included in the generation apparatus 10. For example, the processor 10d reads, from the HDD 10b or the like, a program that has functions similar to those of the determining unit 101, the transform unit 102, the generation unit 103, and the assigning unit 104. The processor 10d executes the process for executing processing similar to that of the determining unit 101, the transform unit 102, the generation unit 103, and the assigning unit 104.

As described above, the generation apparatus 10 operates as an information processing apparatus that performs a learning classification method by reading and executing a program. The generation apparatus 10 may also implement functions similar to those of the embodiment described above by reading the program from a recording medium with a medium reading device and executing the read program. The program in other embodiments is not limited to a program executed by the generation apparatus 10. For example, the present disclosure may be similarly applied to a case where an other computer or a server executes the program, or a case where the other computer and the server execute the program in cooperation with each other.

This program may be distributed via a network such as the Internet. This program may be recorded on a computer-readable recording medium such as a hard disk, a flexible disk (FD), a compact disc read-only memory (CD-ROM), a magneto-optical disk (MO), or a digital versatile disc (DVD) and may be read from the storage medium and executed by a computer.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A non-transitory computer-readable storage medium storing a program that causes a computer to execute a process, the process comprising:
    determining a first filter processing that was applied to a first image used as training data for machine learning, the first filter processing being associated with a first imaging condition that is an imaging condition of the first image;
    generating, by applying a second filter processing, different from the first filter processing, to the first image from which characteristics of the first filtering process are removed, the second filter processing being associated with a second imaging condition that is different from the first imaging condition, a second image to be used in the machine learning as the training data; and
    assigning, to the second image, a label identical to a label of the first image.

2. The non-transitory computer-readable storage medium according to claim 1, wherein the process comprising
    performing the machine learning by using pair data in which the second image and the label identical to the label of the first image are associated.

3. The non-transitory computer-readable storage medium according to claim 1, wherein
    determining includes determining a first point spread function of the first filter processing that was applied to the first image by a convolution operation;
    generating of the first image includes generating the first image that is transformed into a frequency domain by Fourier transform and from which the characteristics of the first point spread function are removed by multiplication; and
    generating of the second image includes generating, as the second image, an image obtained by transforming, into a time domain by inverse Fourier transform, a result obtained by applying, by multiplication, a second point spread function transformed into a frequency domain by Fourier transform, to the first image from which the characteristics are removed as the second filter processing.

4. The non-transitory computer-readable storage medium according to claim 1, wherein
    determining includes determining the first filter processing associated with the first imaging condition that is a combination of an imaging apparatus and a reconstruction function used for the first image, and
    generating of the second image includes generating, as the second image, an image obtained by applying the second filter processing associated with the second imaging condition that is a combination of an imaging apparatus and a reconstruction function and is different from the first imaging condition, to the first image in which the characteristics of the first filter processing are canceled.

5. The non-transitory computer-readable storage medium according to claim 1, wherein
    assigning includes assigning, to the second image, a correct label, for machine learning, assigned to the first image.

6. The non-transitory computer-readable storage medium according to claim 5, wherein
    assigning includes assigning, to the second image, a correct label that corresponds to a case and is assigned to the first image that is a computed tomography image of a human body.

7. A training data generation method executed by a computer, the method comprising:
    determining first filter processing that was applied to a first image used as training data for machine learning, the first filter processing being associated with a first imaging condition that is an imaging condition of the first image;

generating the first image from which characteristics of the determined first filter processing are removed;

generating, by applying a second filter processing, different from the first filter processing, to the first image from which characteristics of the determined first filter processing are removed, the second filter processing being associated with a second imaging condition that is different from the first imaging condition, a second image to be used in the machine learning as the training data; and assigning, to the second image, a label identical to a label of the first image.

8. The method according to claim 7, further comprising performing the machine learning by using pair data in which the second image and the label identical to the label of the first image are associated.

9. The method according to claim 7, wherein
determining includes determining a first point spread function of the first filter processing applied to the first image by a convolution operation;
generating of the first image includes generating the first image that is transformed into a frequency domain by Fourier transform and from which the characteristics of the first point spread function are removed by multiplication; and
generating of the second image includes generating, as the second image, an image obtained by transforming, into a time domain by inverse Fourier transform, a result obtained by applying, by multiplication, a second point spread function transformed into a frequency domain by Fourier transform, to the first image from which the characteristics are removed as the second filter processing.

10. The method according to claim 7, wherein
assigning includes assigning, to the second image, a correct label, for machine learning, assigned to the first image.

11. The method according to claim 10, wherein
assigning includes assigning, to the second image, a correct label that corresponds to a case and is assigned to the first image that is a computed tomography image of a human body.

12. The method according to claim 7, wherein
the first imaging condition is a first combination of an imaging apparatus and a reconstruction function used for the first image, and
the second imaging condition that is a second combination of an imaging apparatus and a reconstruction function, the second combination being different from the first combination.

13. A training data generation apparatus, comprising:
a memory; and
a processor coupled to the memory, the processor configured to:
determine a first filter processing that was applied to a first image used as training data for machine learning, the first filter processing being associated with a first imaging condition that is an imaging condition of the first image,
generate the first image from which characteristics of the determined first filter processing are removed, and
generate, by applying a second filter processing, different from the first filter processing, to the first image from which the characteristics are removed, the second filter processing being associated with a second imaging condition that is different from the first imaging condition, a second image to be used in the machine learning as the training data; and
assign, to the second image, a label identical to a label of the first image.

14. The training data generation apparatus according to claim 13, wherein the processor is further configured to:
perform the machine learning by using pair data in which the second image and the label identical to the label of the first image are associated.

15. The training data generation apparatus according to claim 13, wherein the processor is further configured to:
determine the first filter processing by determining a first point spread function of the first filter processing that was applied to the first image by a convolution operation;
generate the first image transformed into a frequency domain by Fourier transform and from which the characteristics of the first point spread function are removed by multiplication; and
generate the second image transformed into a time domain by inverse Fourier transform, a result obtained by applying, by multiplication, a second point spread function transformed into a frequency domain by Fourier transform, to the first image from which the characteristics of the first point spread function are removed, as the second filter processing.

16. The training data generation apparatus according to claim 13, wherein the processor is further configured to:
assign, to the second image, a correct label, for machine learning, assigned to the first image.

17. The training data generation apparatus according to claim 16, wherein the processor is further configured to:
assigning, to the second image, a correct label that corresponds to a case and is assigned to the first image that is a computed tomography image of a human body.

18. The training data generation apparatus according to claim 13, wherein
the first imaging condition is a first combination of an imaging apparatus and a reconstruction function used for the first image, and
the second imaging condition that is a second combination of an imaging apparatus and a reconstruction function, the second combination being different from the first combination.

* * * * *